US011350872B1

(12) United States Patent
Schoess et al.

(10) Patent No.: US 11,350,872 B1
(45) Date of Patent: Jun. 7, 2022

(54) FOOTSMART MAT

(71) Applicant: EDEN MEDICAL, INC., Howard Lake, MN (US)

(72) Inventors: Jeffrey Norman Schoess, Howard Lake, MN (US); David G Armstrong, Studio City, CA (US)

(73) Assignee: EDEN MEDICAL. INC, Howard Lake, MN (US)

( * ) Notice: Subject to any disclaimer, the term of this patent is extended or adjusted under 35 U.S.C. 154(b) by 0 days.

(21) Appl. No.: 17/525,853

(22) Filed: Nov. 12, 2021

Related U.S. Application Data

(60) Provisional application No. 63/113,053, filed on Nov. 12, 2020.

(51) Int. Cl.
*A61B 5/1455* (2006.01)
*A61B 5/01* (2006.01)
*A61B 5/00* (2006.01)

(52) U.S. Cl.
CPC ............ *A61B 5/447* (2013.01); *A61B 5/0075* (2013.01); *A61B 5/0077* (2013.01); *A61B 5/443* (2013.01); *A61B 5/445* (2013.01); *A61B 2562/066* (2013.01); *A61B 2562/164* (2013.01)

(58) Field of Classification Search
CPC ............ A61B 5/14551; A61B 5/14542; A61B 5/14552; A61B 5/6829; A61B 5/0075; A61B 5/4842; A61B 5/447; A61B 5/7275
See application file for complete search history.

(56) References Cited

U.S. PATENT DOCUMENTS

2013/0261494 A1* 10/2013 Bloom ................. A61B 5/6807
600/549

* cited by examiner

*Primary Examiner* — Jon Eric C Morales
(74) *Attorney, Agent, or Firm* — Underwood & Associates, LLC

(57) ABSTRACT

A system for predicting an occurrence of a foot ulcer includes a mat configured to be stood upon by a human subject, a plurality of sensor arrays disposed on or in said mat and arranged in adjacent proximity to one another. Each sensor includes an oxygenation probe, itself including a first light source and a light detector, and a secondary probe operable to utilize the light detector of the oxygenation probe and itself including a plurality of light sources exclusive of the first light source. The plurality of light sources of the secondary probe are arranged in a pattern around the oxygenation probe. The oxygenation probe is located at the approximate geometric center of the pattern. The system further includes a control module in signal communication with the light detector, and configured to independently control emission of light from the first light source of the oxygenation probe and the plurality of light sources of the secondary probe.

20 Claims, 9 Drawing Sheets

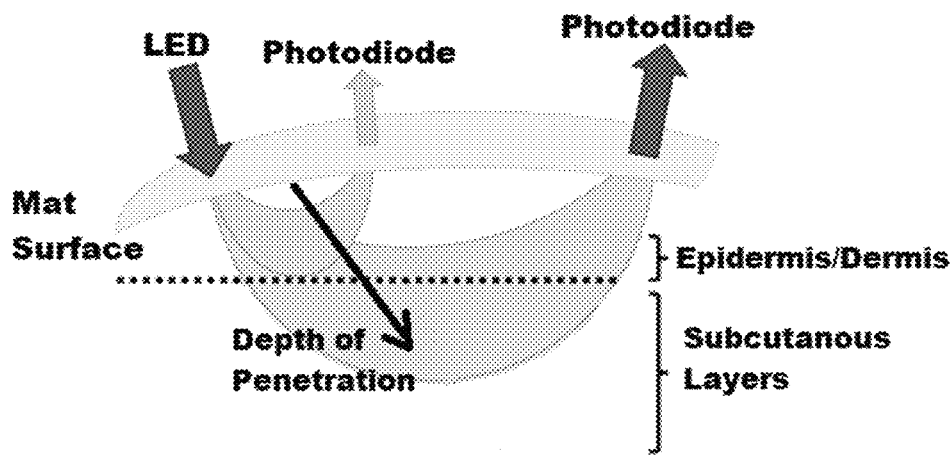

FIG. 5

$$\Delta HbO_2 = \frac{\log\frac{I^b(\lambda_{730nm})}{I^s(\lambda_{730nm})}\varepsilon_{deoxy}(\lambda_{850nm}) - \log\frac{I^b(\lambda_{850nm})}{I^s(\lambda_{850nm})}\varepsilon_{deoxy}(\lambda_{730nm})}{L[\varepsilon_{oxy}(\lambda_{730nm})\varepsilon_{deoxy}(\lambda_{850nm}) - \varepsilon_{oxy}(\lambda_{850nm})\varepsilon_{deoxy}(\lambda_{730nm})]} \quad (1.1)$$

$$\Delta Hb = \frac{\log\frac{I^b(\lambda_{850nm})}{I^s(\lambda_{850nm})}\varepsilon_{oxy}(\lambda_{730nm}) - \log\frac{I^b(\lambda_{730nm})}{I^s(\lambda_{730nm})}\varepsilon_{oxy}(\lambda_{850nm})}{L[\varepsilon_{oxy}(\lambda_{730nm})\varepsilon_{deoxy}(\lambda_{850nm}) - \varepsilon_{oxy}(\lambda_{850nm})\varepsilon_{deoxy}(\lambda_{730nm})]} \quad (1.2)$$

FIG. 6

FOOTSMART MAT

CROSS REFERENCE TO RELATED APPLICATIONS

This application claims priority to and the benefit under 35 USC § 119(e) of U.S. Provisional Patent Application No. 63/113,053, filed on Nov. 12, 2020 under the same application title, the contents of which are incorporated by reference in their entirety as if fully set forth herein.

STATEMENT REGARDING FEDERALLY SPONSORED RESEARCH OR DEVELOPMENT

None.

TECHNICAL FIELD

This disclosure relates to systems and methods for predicting an occurrence of a diabetic foot, or pressure ulcer in a human subject.

BACKGROUND

More individuals are now dying of chronic non-communicable diseases (NCD) than acute diseases associated with disasters, trauma, or infection. Diabetes is the quintessential NCD. The long neglected diabetic foot ulcer (DFU) ranks among the most debilitating and costly sequela of this syndrome in the world.

Diabetes around the globe results in one major limb amputation every 20 seconds, over 2500 limbs lost per day. On the basis of 2015 prevalence data from the International Diabetes Federation, it is estimated that, annually, foot ulcers develop in 9.1 million to 26.1 million people with diabetes worldwide. The proportion of persons with diabetes and a history of foot ulceration is understandably higher than the proportion with an active ulcer; 3.1 to 11.8% of persons with diabetes, or 12.9 million to 49.0 million persons worldwide and 1.0 million to 3.5 million in the United States alone, have a history of foot ulceration.

In 2012, the total cost of diabetes was $245 billion, a 41% increase from 2007. In the US, one-third of diabetes-related costs are spent on DFU and wound healing. The national cost of $1.9 billion per year is for emergency treatment of DFUs and $8.78 billion per year for inpatient costs.

The recurrence of a foot ulcer is common. The incidence rates for ulcer recurrence is roughly 40% of patients have a recurrence within 1 year after ulcer healing, almost 60% within 3 years, and 65% within 5 years. The lifetime incidence of foot ulcers has been estimated to be 15 to 25% among persons with diabetes.

The natural history of a diabetes-related foot ulcer is sobering. The risk of death at 5 years for a patient with a diabetic foot ulcer is 2.5 times as high as the risk for a patient with diabetes who does not have a foot ulcer. More than half of diabetic ulcers become infected. Approximately 20% of moderate or severe diabetic foot infections lead to some level of amputation. There is room for improvement in the effective management of DFUs, reducing risk of reulceration. Accordingly, an intuitive and user-friendly diagnostic tool for the prediction of a new or recurring foot ulcer is an unmet need in the arts.

SUMMARY

In general, systems and methods for the prediction of new or recurring foot ulcers are disclosed.

In a first aspect, a system for predicting an occurrence of a foot ulcer includes a mat, such as a floor mat, configured to be stood upon by a human subject, a plurality of sensor arrays disposed on or in the mat and arranged in adjacent proximity to one another. Each sensor includes an oxygenation probe including a first light source and a light detector. The system further includes a secondary probe operable to utilize the light detector of the oxygenation probe and includes a plurality of light sources exclusive of the first light source, the plurality of light sources being arranged in a pattern. The oxygenation probe is located at the approximate geometric center of the pattern. The system further includes a control module in signal communication with the light detector, which is configured to independently control emission of light from the first light source of the oxygenation probe and the plurality of light sources of the secondary probe.

In one embodiment, the light detector is configured to measure an amount of light that propagates from at least one of the plurality of light sources of the secondary probe, through a region of foot tissue of the human subject, to the light detector.

In one embodiment, the number of sensor arrays are disposed and arranged on a planar surface.

In one embodiment, the first light source, and each of the light sources of the secondary probe are configured to emit light perpendicular to the planar surface.

In one embodiment, the planar surface is configured to receive a bottom surface of a human foot, or to be placed on a bottom surface of a human foot.

In one embodiment, the secondary probe includes between four and 10 of the light sources. The light sources of the secondary probe can be arranged in a square or circle around the oxygenation probe.

In one embodiment, the system further includes an inertial measurement unit, a temperature sensor, and a pressure sensor in signal communication with the control module and disposed on or in the mat.

In one embodiment, the oxygenation probe includes an area of about one centimeter.

In one embodiment, the number of light sources of the secondary probe are located about one centimeter from the oxygenation probe.

In one embodiment, the light sources of the secondary array are configured to emit light in the near infrared portion of the electromagnetic spectrum. The light sources of the secondary array can be configured to emit at least two different wavelengths of light, such as a first wavelength of 730 nm and a second wavelength of 850 nm.

In one embodiment, the system further includes a computer processor in signal communication with an analysis module, a memory and an input/output module, wherein the input/output module is in signal communication with the number of sensor arrays. The analysis module can be configured to differentiate ulcerous foot tissue from surrounding healthy foot tissue.

In a second aspect, a method for predicting an occurrence of a diabetic foot ulcer is disclosed. The method includes providing a system for predicting an occurrence of a foot ulcer as described herein, receiving the bottom portion of the human subject's foot upon the mat, generating a map of measured oxygenation on the plantar, mid-foot or heel region of the foot utilizing the system, identifying, from the map, target regions of potential ulceration in the foot measured by the plurality of oxygenation probes, and interrogating the target regions of potential ulceration by generating a map of oxyhemoglobin within the foot utilizing the secondary probes.

In one embodiment, the method further includes determining the estimated difference index in oxyhemoglobin concentration between an area probed by the oxygenation probe and an area probed by the secondary probe. If the estimated difference index is a positive value, it can indicate an area of inflammation or hyperperfusion. If the estimated difference index is a negative value, it can indicate an ischemic or hypervascularization condition.

In one embodiment, the method further includes a plurality of temperature sensors, and wherein the temperature sensors are utilized to determine regions of temperature asymmetry between the feet of the human subject. If a region of temperature asymmetry is determined, the region can be utilized as an initial target for generating the map of oxyhemoglobin within the foot.

Certain advantages of the systems and methods disclosed herein include the potential to predict recurring ulcer formation, to reduce the cost of treatment (e.g., hospitalization, loss of work), to reduce discomfort and pain, and increase walking efficiency.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings, which may not necessarily be to scale, in which like references indicate similar elements, and in which:

FIG. 5 illustrates light propagation through a medium, according to one embodiment;

FIG. 6 shows NIRS algorithms for quantifying changes in $HbO_2$ and Hb according to one embodiment;

DETAILED DESCRIPTION OF ILLUSTRATIVE EMBODIMENTS

Figure 1:
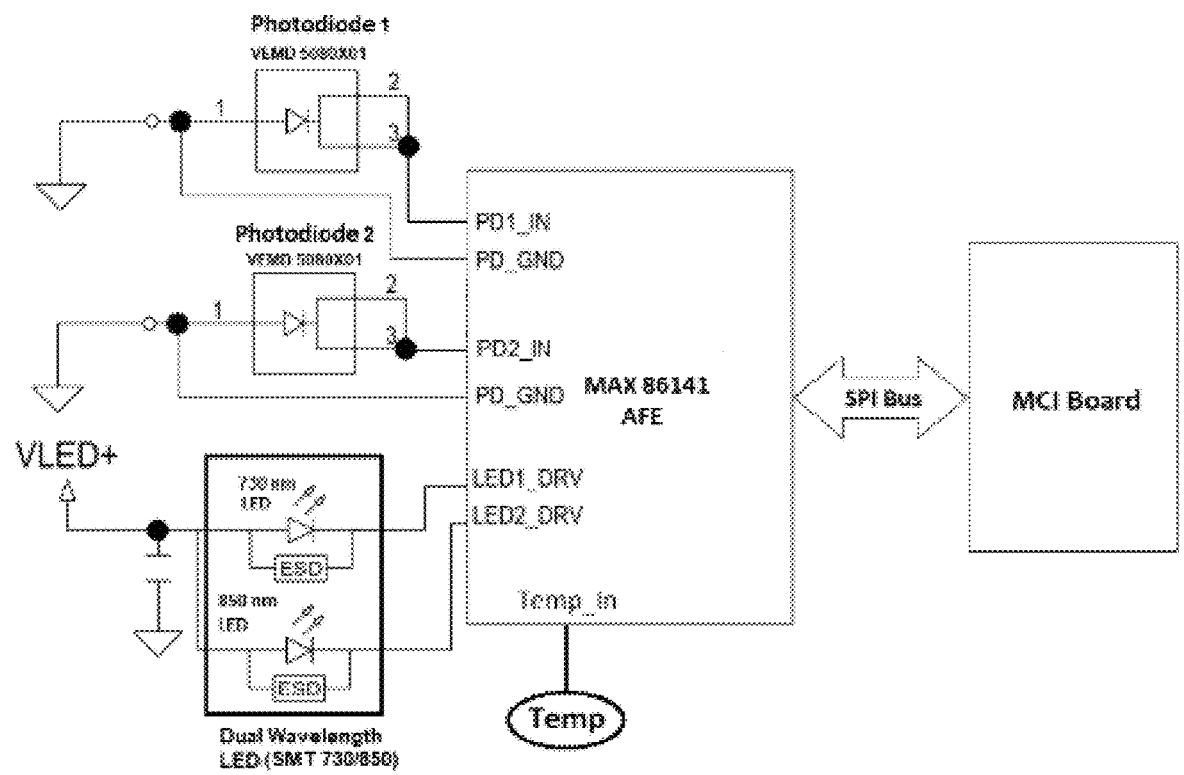
FIG. 1 illustrates exemplary circuitry and LED controls of a system for predicting an occurrence of a foot ulcer, according to one embodiment.
Figure 2:
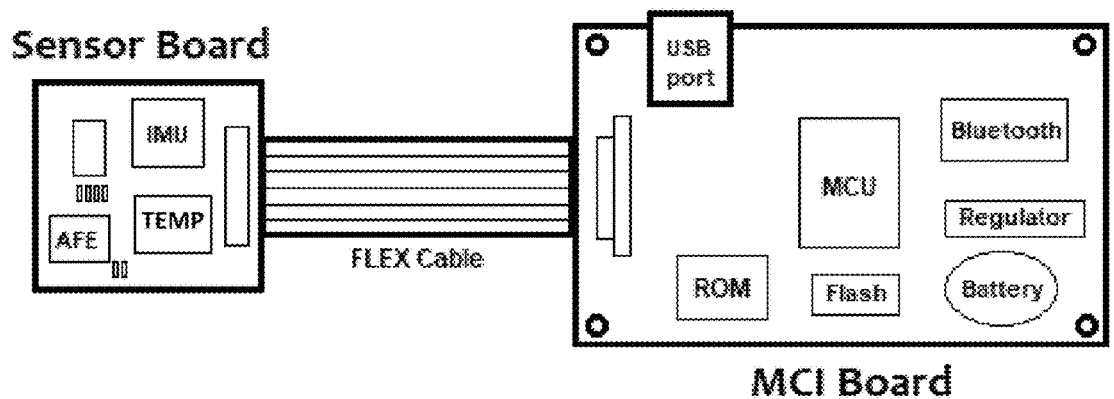
FIG. 2 shows a sensor board layout with an analog front end according to one embodiment.
Figure 3:
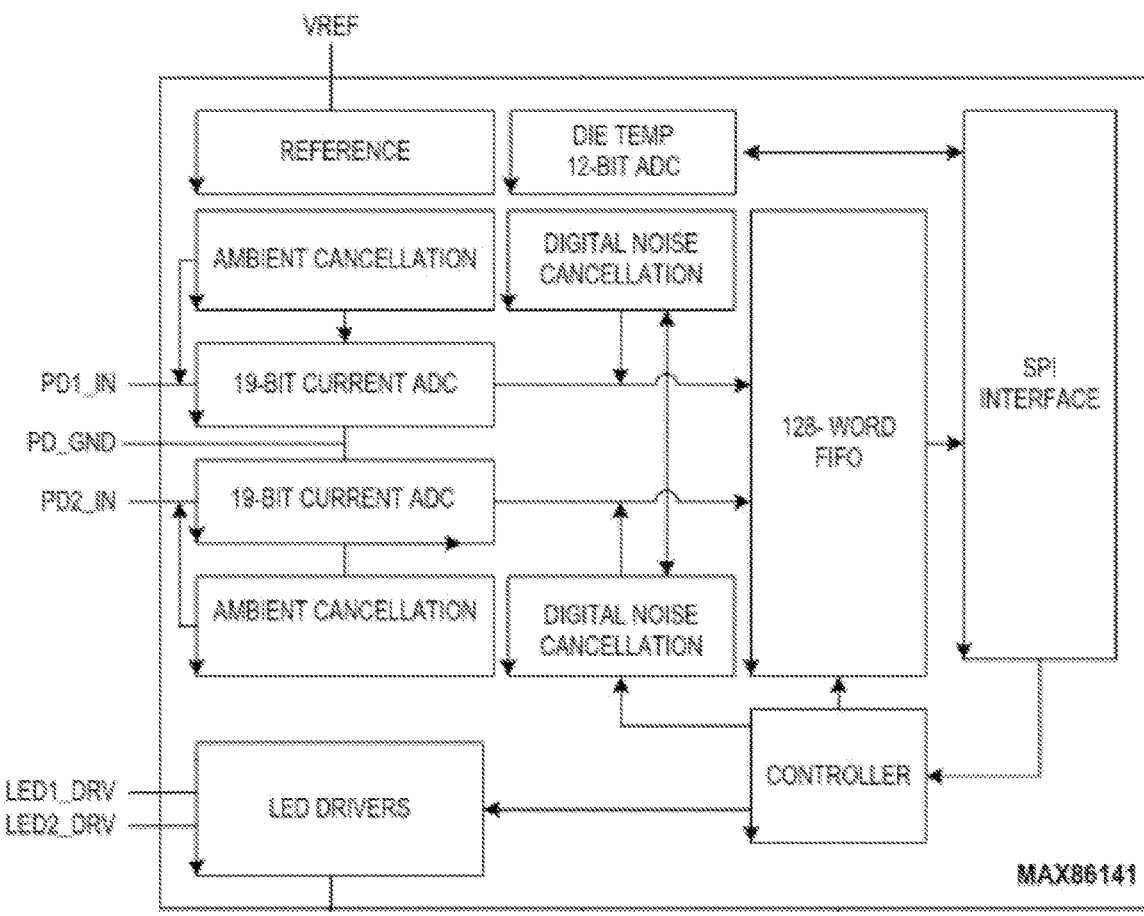
FIG. 3 shows an exemplary analog front end integrated circuit, according to one embodiment.

FIG. 1 illustrates exemplary circuitry and LED controls of a system for predicting an occurrence of a foot ulcer (colloquially termed a 'FootSmart Mat'). In this embodiment, the diagram features a microcontroller unit (MCU) circuit board to control the data acquisition process and a sensor daughter board. The sensor board is electrically connected to the MCU board via a flex circuit cable to provide sensor commands and acquire optical sensor data. The MCU board communicates with the sensor daughter board via the serial peripheral bus (SPI). FIG. 2 shows the sensor board layout with the analog front end (AFE). The sensor board has an analog front end (AFE) IC, inertial measurement unit (IMU), two near infrared LEDS, temperature sensor, pressure sensor and photodiodes. An exemplary AFE IC is shown in FIG. 3.

The AFE features a two-channel data acquisition system, programmable LED driver (four full scale ranges, 32, 64, 93, and 124 ma) to drive the two LEDs (i.e. 730 and 850 nm), two optical readout channels (two photodiode interface), first-in-first out (FIFO) memory, and two 19-bit A/Ds. The MCU board contains the microcontroller IC to acquire the data, a wireless Bluetooth interface for user interface support, built-in read only (ROM) and random-access (RAM) memory and battery management. The optical channel has 4 full scale ranges. These ranges are 4 to 32 µA. It has dual LED drivers, two photodiodes to capture the near infrared light, and SPI bus interface.

Figure 4:
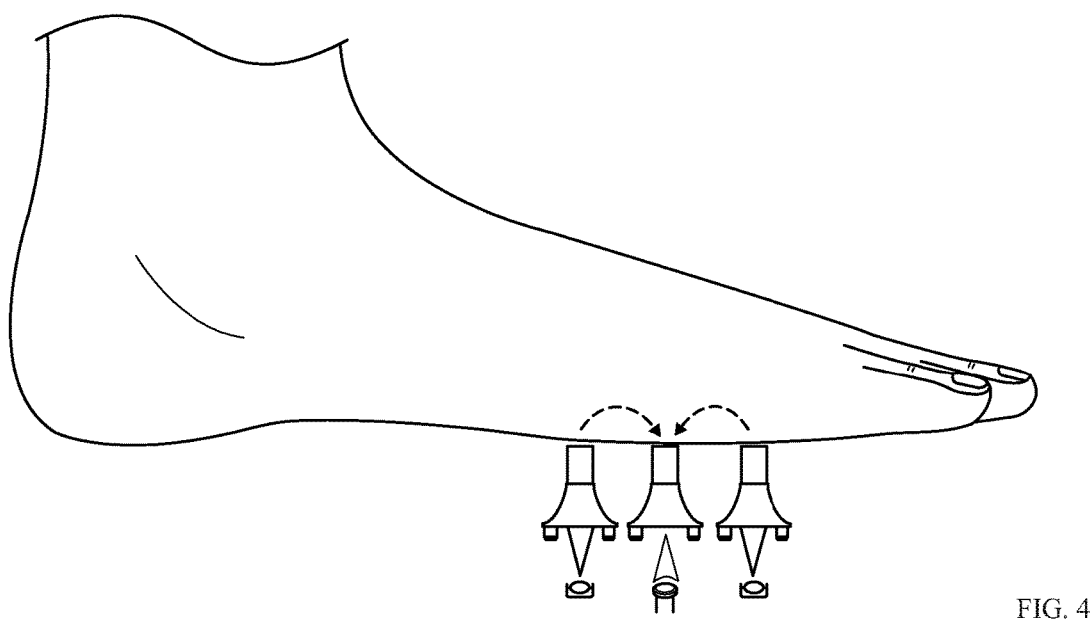
FIG. 4 illustrates a FootSmart Mat concept according to one embodiment.

FIG. 4 illustrates a FootSmart Mat concept according to one embodiment. A 730 nm LED (red, far left) is shown projecting light into a lightpipe which transmits the light and focuses it into a subject's foot. A second 850 nm LED (red, far right) is also shown with its lightpipe, and a photodiode is located between the two LEDs (blue, center). The red collar shown around each LED holds the lightpipe in place and is mounted on the sensor board. The blue color collar retains the lightpipe for the photodetector. The LEDs and photodiode will be organized as a sensor array to measure hemoglobin biomarkers $HbO_2$ and $StO_2$.

Lightpipes can be fabricated with, e.g., acrylic, polycarbonate or Pyrex. Polycarbonate is stronger with higher impact resistance but is susceptible to scratching. Acrylic offers the benefits of ease of fabrication (i.e. cutting, polishing to remove scratches), while Pyrex is has the highest transmittance (94-95% vs. 90% for Acrylic).

Referring now to FIG. 5, without wishing to be bound by theory, it is postulated based on known research that near infrared light projected into foot tissue will propagate in a semi-arcuate path, illustrated by the blue and green zones. The Beer-Lambert law (hereinafter the law') predicts a linear relationship between absorbance (transmittance) of NIRS light and measuring the concentration of oxyhemoglobin. The molar extinction coefficient (c) is a measure of how strongly oxyhemoglobin absorbs light at a particular wavelength in units of $M^{-1}$ $cm^{-1}$ where the optical path length is in centimeters. The law defines the depth of penetration to be one-half the distance between the LED and photodetector. Effective penetration of light is also determined by several other factors: wavelength of light, attenuation coefficient (scattering, refraction, and absorption), area of irradiance (power density-watts/cm$^2$).

The NIRS algorithms for quantifying changes in $HbO_2$ and Hb is shown FIG. 6 in equation 1.1 and 1.2 therein. $I^S(\lambda x)$ is the intensity of light at wavelength 'x' during transmission. $I^b(\lambda x)$ is the measure of light during baseline (with no light transmission) or the ambient light. $\varepsilon_{oxy}(\lambda x)$ is the extinction coefficient for $HbO_2$ at wavelength 'x' and $\varepsilon_{deoxy}(\lambda x)$ is the extinction coefficient for Hb at wavelength 'x'. L is the optical path length between the LED and photodetector. The oxygenation saturation (%) is calculated as: $(HbO_2/HbO_2+Hb)\times 100$. The light pipe provides effective flux coupling projecting the light with minimum flux loss. The losses include LED insertion (Fresnel) loss (up to 4% loss,) light leakage out the pipe wall (10% loss), and pipe exit Fresnel loss (4%). The radiation pattern at the pipe exit can be designed to maximize on-axis intensity and a narrow radiation pattern with a small viewing angle.

In this embodiment, a dual wavelength bi-color LED is used. It features peak wavelength operation at 730 nm and 850 nm. Its radiated power is 24 mw at 50 ma and 230-360 mw of pulsed power output. It is packaged in a small surface mount package. The LED has a wide radiation field of +/−62 degrees to provide the best flux capture. A PIN photodiode (Vishay Semi VEMD5060X01) has been selected, is packaged as a surface mount device with a 7.5 mm$^2$ sensitive area. It has a high responsivity of 64 mV/(microwatt/cm2).

Figure 7:
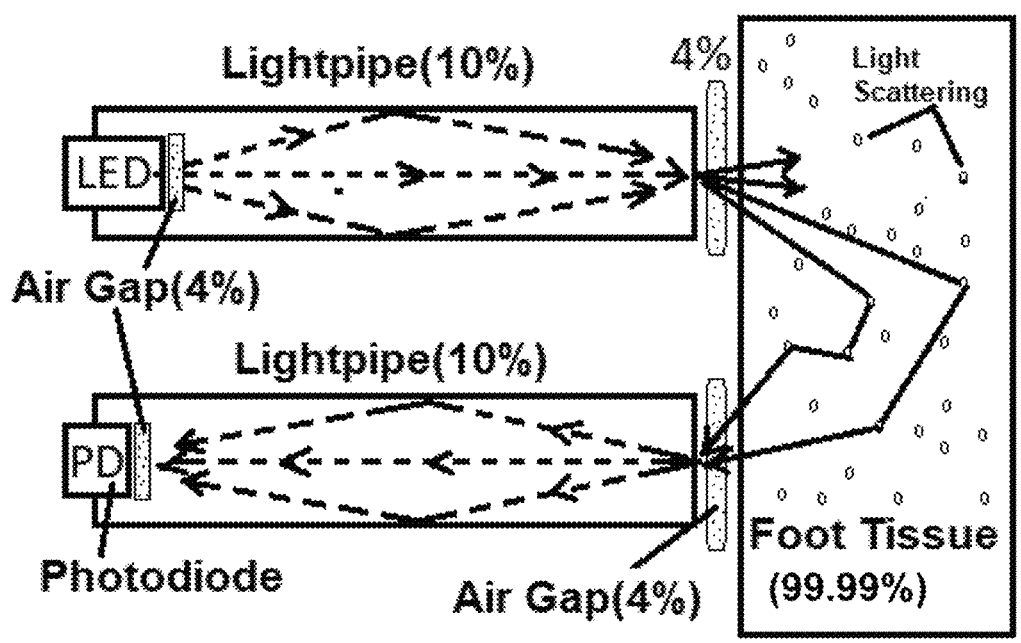
FIG. 7 shows an exemplary light-tissue interaction model.

Without wishing to be bound by theory, a proposed light-tissue interaction model is shown in FIG. 7. In this embodiment, the LED emits near infrared light in the lightpipe and projects it into the tissue of the foot. The light is absorbed, scattered and reflected back into a second light pipe, and detected by the photodiode. An in-house bench test optical power analysis indicates that an LED operating at 124 ma (310 mW) can project 1,150 mw/cm$^2$ power output at the lightpipe output. It was determined that 0.791 mw/cm2 of optical power can be available at the photodiode detector, which was estimated to produce 19.0 μA of output current.

Loss of light through a living human hand (mid-palm penetration of 25 mm at 830 nm, Omnilux New-U low-level planar array light therapy source, 500 mW) have been measured previously at a rate of 99.99%. The average thickness of skin on the bottom of the foot is 1.5 mm This indicates a NIR penetration level of 2 mm should be adequate to detect any recurring foot ulcer with an average skin thickness of 1.5 mm. Thicker penetration depths may be required due to wound formation into subcutaneous tissue which will reduce optical power.

Figure 8:
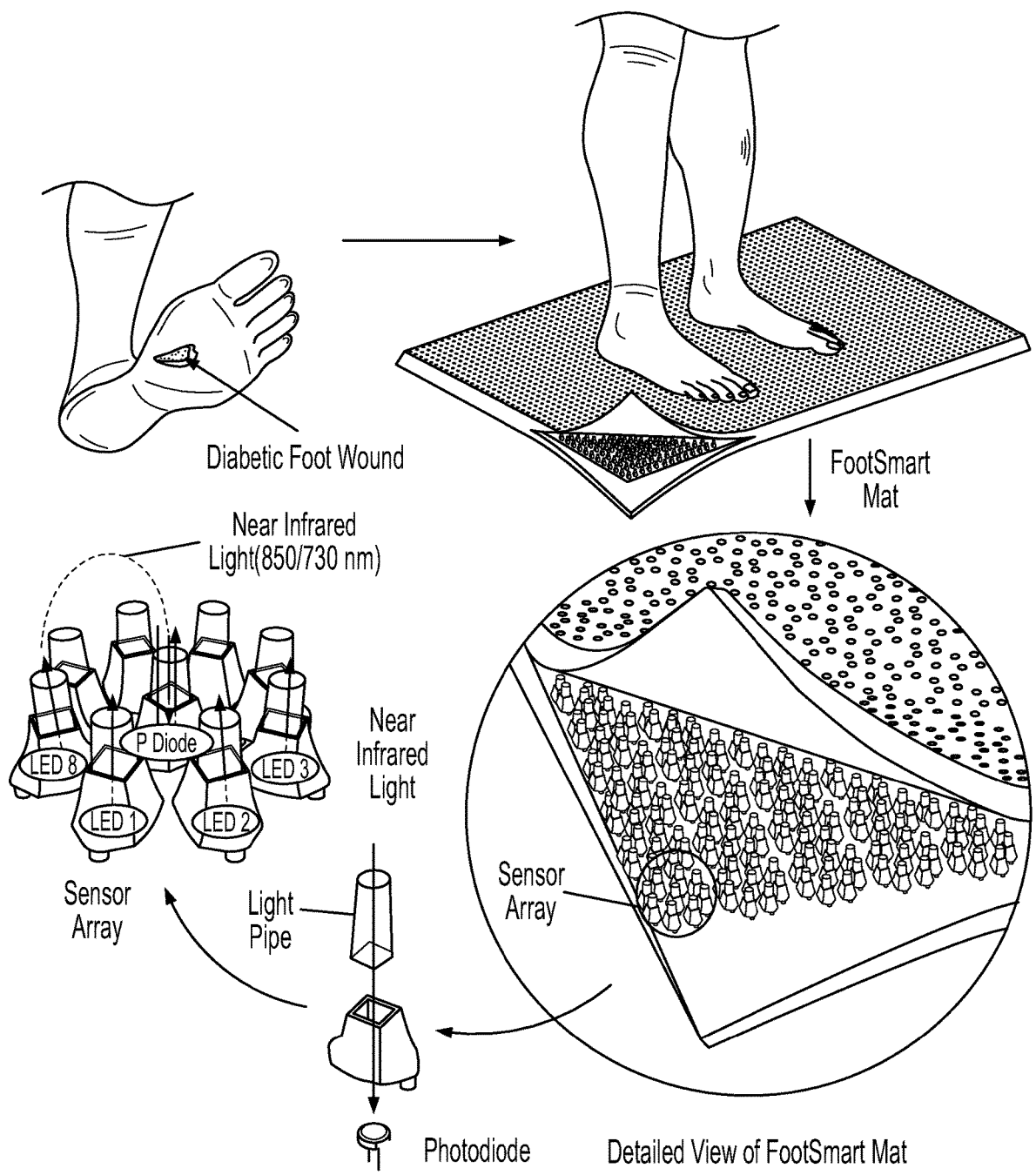
FIG. 8 illustrates a system (FootSmart Mat') for measuring and quantifying hemoglobin biomarkers of $HbO_2$ and $StO_2$ associated with oxygen delivery, according to one embodiment.

Referring now to FIG. 8, a system (FootSmart Mat') for measuring and quantifying hemoglobin biomarkers of $HbO_2$ and $StO_2$ associated with oxygen delivery is shown according to one embodiment. In this embodiment, the mat will also have integrated temperature sensors to detect temperature asymmetry between both feet.

In this embodiment, In this embodiment, the target area is about 1.0 cm in diameter, a typical size of a DFU. In the center of the sensor array (the target area) an LED pair and photodiode, cooperatively "an oxygenation probe", is located adjacent of each other.

Figure 9:
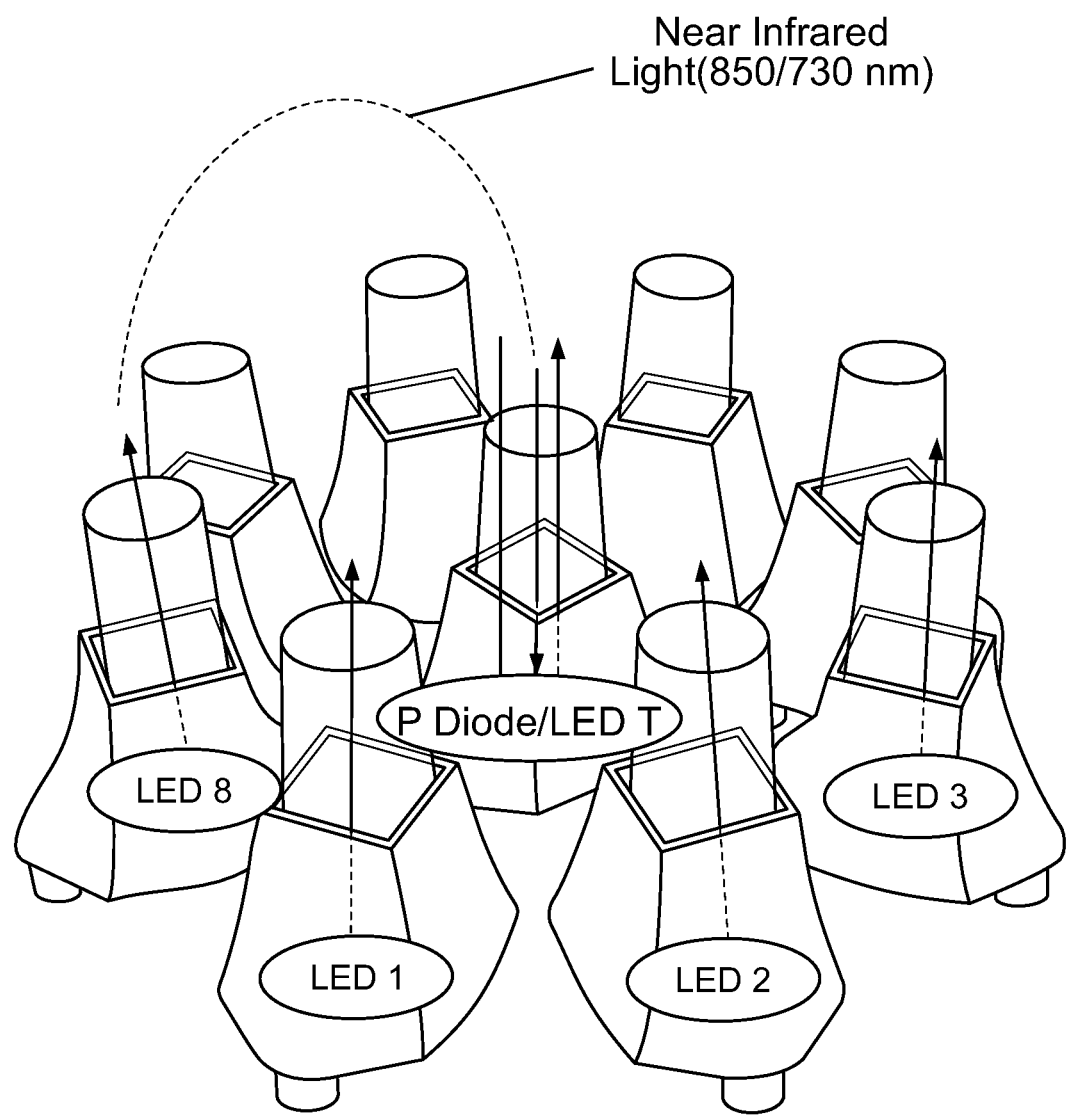
FIG. 9 shows an exemplary sensor of the system, according to one embodiment.

A set of NIRS sensor arrays will generate oxyhemoglobin ($HbO_2$) and tissue oxygen saturation ($StO_2$) maps. Each sensor array can have a number of sensor pairs, e.g., 4, 5, 6, 7, 8, 9, 10 pairs; in this example, the system has 8 LED pairs that emit light at 730 nm and 850 nm and are arranged in a ring outside the recurring ulcer target area as shown in FIG. 9. As used herein, the LED pairs (8, in this example), and the photodiode of the oxygenation probe, are collectively referred to as a "secondary probe."

In one embodiment, a measurement of oxygenation includes first measuring $HbO_2$ and Hb in the target area using the oxygenation probe. The LEDs in the outer ring of the array will then be sampled capturing adjacent region data around the target area (i.e., using the secondary probe).

Figure 10:
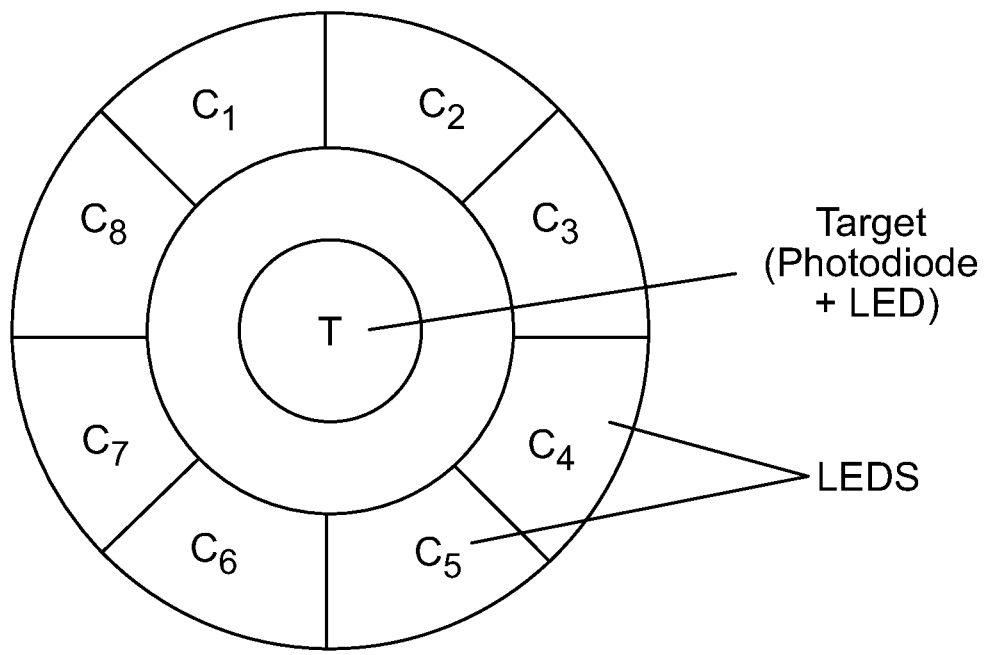
FIG. 10 illustrates an exemplary map layout according to one embodiment.

In doing so, infrared light is projected through each dedicated lightpipe into the foot tissue, and captured by the photodiode in the target area as shown in FIG. 9. This method will generate a map of oxyhemoglobin. The map layout is illustrated in FIG. 10 with the target area in the center and LEDs surrounding the target area. The inner rim of the adjacent region will be 1 cm from the outer rim of the target region. The radius of the outer rim of the adjacent region has been chosen such that the surface area of each of the eight segments are the same as the target area and equal to 0.79 cm$^2$.

The estimated difference (ED) index in oxyhemoglobin concentration (O) between the target (T) and the adjacent regions are defined as: ED=OT−OA where OT is the oxyhemoglobin in the target area and OA is the oxyhemoglobin in the adjacent area. If the ED index is a positive value, this may indicate inflammation (i.e. indicating hyperperfusion) exists between the target area and adjacent regions. If the ED index is a negative value, an ischemic condition may exist with hypervascularization occurring in the recurring ulcer site.

Figure 11:
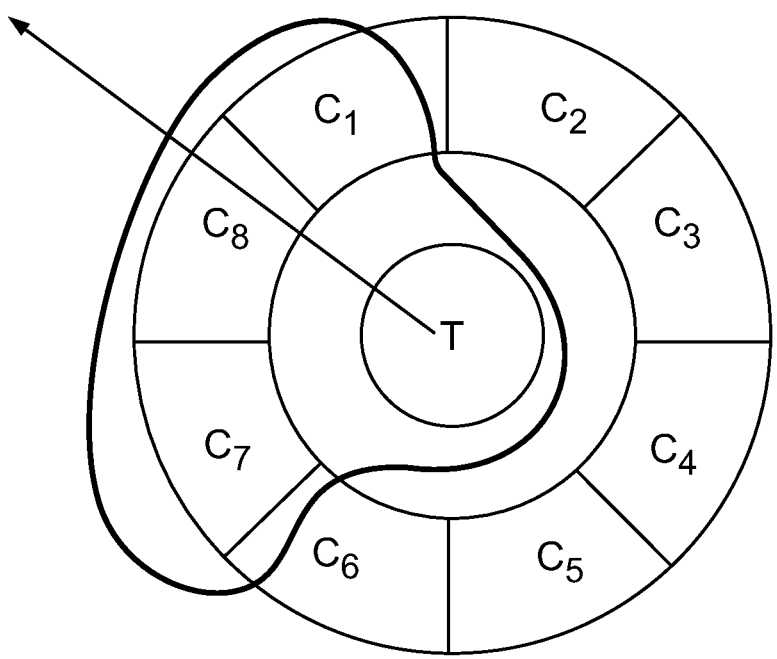
FIG. 11 illustrates a Three-Zone vector for inflammation detection.

In addition, it has been determined that a predictive vector of inflammation or ischemia can be generated by adding the oxyhemoglobin values in adjacent regions. For example, FIG. 11 illustrates a Three-Zone vector for inflammation detection by adding values for each adjacent region (C1, C7, and C8) or ED=OT−(OC1+OC7+OC8). One, two, three, or four zone vectors can be computed. The adjacent area with the highest value in the group, or a weighted sum of the group can determine the direction of the predictive vector.

Figure 12:
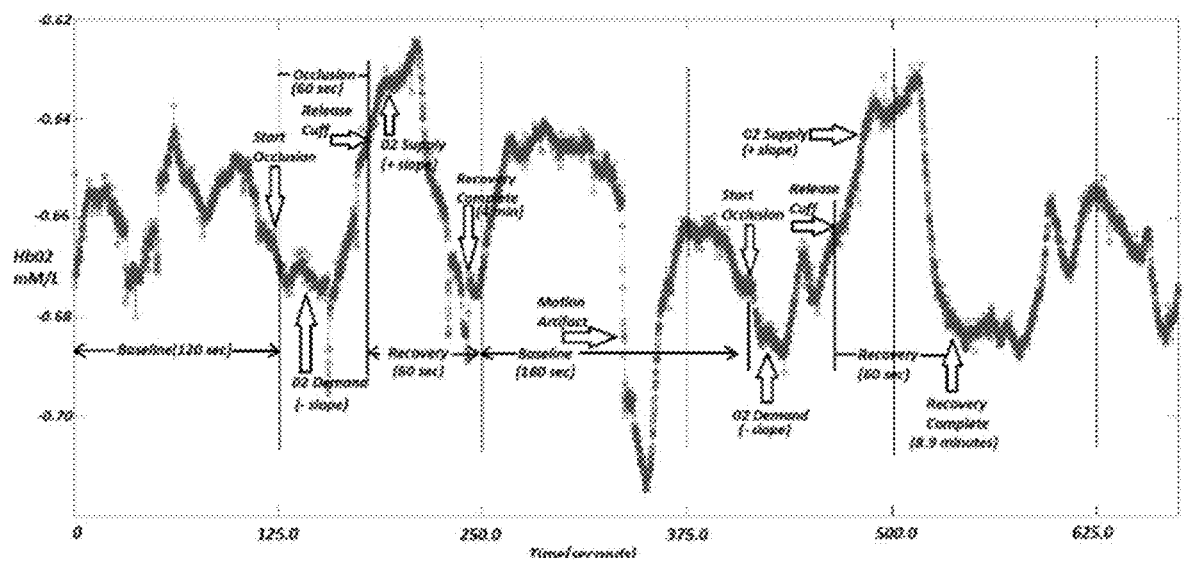
FIGS. 12 and 13 show exemplary occlusion test results obtained by the FootSmart Mat system.
Figure 13:
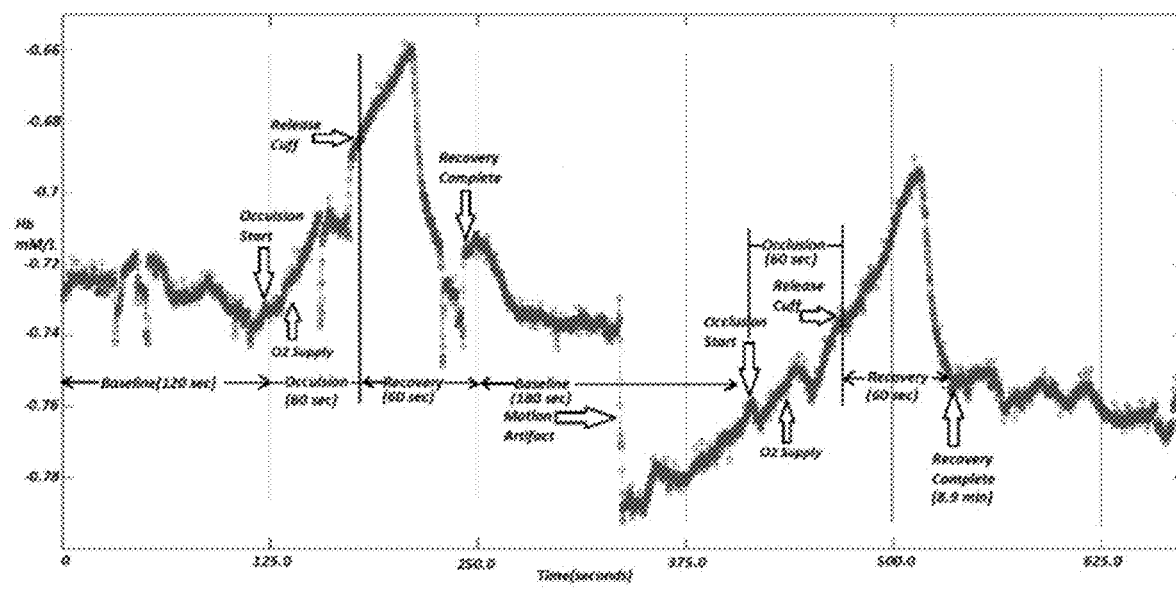

Exemplary occlusion test results are shown in FIGS. 12 and 13 for $HbO_2$ and Hb plots respectively. Two 240-second (i.e. 4-minute) sequential cycles are shown. Each cycle has a 120 second baseline period (no occlusion, sitting at rest) followed by a 60 second occlusion period (160 mmHg applied pressure) and a 60 second recovery period (occlusion cuff pressure is released). The analysis indicates clear indication of $HbO_2$ measurement with an oxygen demand (i.e. extraction) event (i.e. $HbO_2$ decrease) shown after occlusion pressure is applied as indicated by a negative slope output (i.e. 120 and 420 seconds) and an oxygen supply event (i.e. $HbO_2$ supply) shown after occlusion pressure is removed (i.e. positive slope output—180 and 480 seconds).

The data clearly show the loss and recovery of oxyhemoglobin as a two-step process. The Hb measurement shows a similar response except a positive slope measurement due to application of occlusion pressure. These data indicate several advantages (of many) of the present system and method: 1) it is sensitive enough to track oxygen supply/demand (extraction); 2) a wide dynamic range of the system is 96 dB (16-bit resolution) is demonstrated; 3) the responsivity (i.e. input-output gain) of the photodetector system is adequate to detect the hemoglobin biomarkers for the diabetic subject.

An occlusion test on a type 2 diabetic human subject with has revealed that it is possible with the system disclosed to detect and measure oxyhemoglobin in the plantar region.

Figure 14:
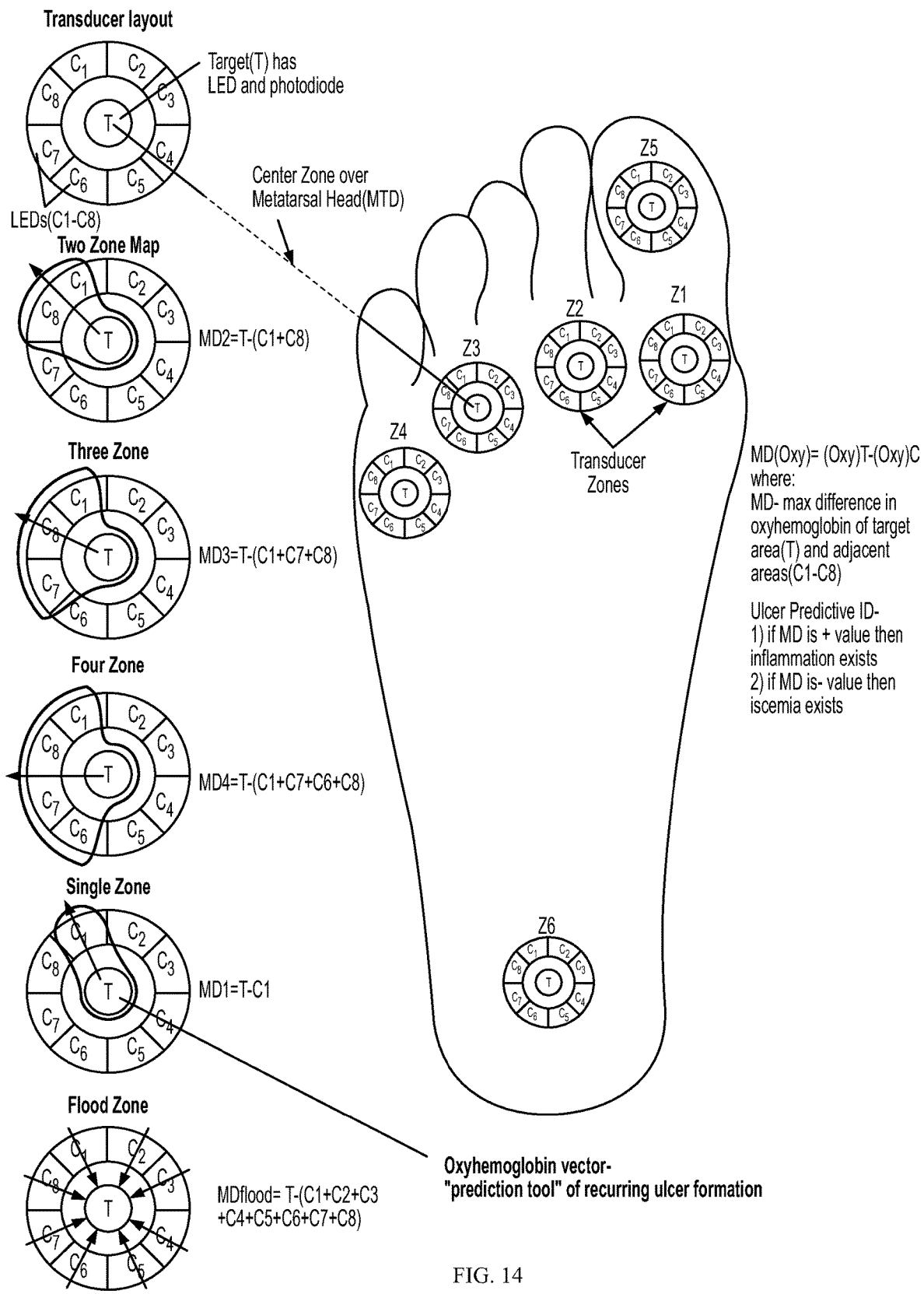
FIG. 14 illustrates a use of the FootSmart Mat system to determine an oxyhemoglobin vector.

Referring now to FIG. 14, in one embodiment, each sensor can be used to determine an oxyhemoglobin vector, which can be used as an interpretive tool for determining physiological pathways of inflammation or ischemia. For example, the two, three, four and single zones depicted in FIG. 14 can be correlated to oxygen flow in the periwound of an ulcer from a particular direction. A flood zone, in comparison can correlate with oxygen flow being directed to the center of the ulcer.

A number of illustrative embodiments have been described. Nevertheless, it will be understood that various modifications may be made without departing from the spirit and scope of the various embodiments presented herein. For example, while the present disclosure has primarily focused on predicting the occurrence of foot ulcers, the same systems and methods can be adapted for predicting pressure ulcers elsewhere on the body, including but not limited to the heel, tailbone, hips or ankles. Accordingly, other embodiments are within the scope of the following claims.

What is claimed is:

1. A system for predicting an occurrence of a foot ulcer, comprising:
    a mat configured to be stood upon by a human subject;
    a plurality of sensor arrays disposed on or in said mat and arranged in adjacent proximity to one another, each sensor comprising:
        an oxygenation probe comprising a first light source and a light detector;
        a secondary probe operable to utilize said light detector of said oxygenation probe and comprising a plurality of light sources exclusive of said first light source, said plurality of light sources being arranged in a pattern;
        wherein said oxygenation probe is located at the approximate geometric center of said pattern; and
    a control module in signal communication with said light detector, and configured to independently control emission of light from said first light source of said oxygenation probe and said plurality of light sources of said secondary probe.

2. The system of claim 1, wherein said light detector is configured to measure an amount of light that propagates from at least one of said plurality of light sources of said secondary probe, through a region of foot tissue of said human subject, to said light detector.

3. The system of claim 1, wherein said plurality of sensor arrays are disposed and arranged on a planar surface.

4. The system of claim 1, wherein each of said first light source, and each of said light sources of said secondary probe are configured to emit light perpendicular to said planar surface.

5. The system of claim 1, wherein said planar surface is configured to receive a bottom surface of a human foot, or to be placed on a bottom surface of a human foot.

6. The system of claim 1, wherein said secondary probe comprises between four and 10 of said light sources.

7. The system of claim 6, wherein said light sources of said secondary probe are arranged in a square or circle around said oxygenation probe.

8. The system of claim 1, further comprising an inertial measurement unit, a temperature sensor, and a pressure sensor in signal communication with said control module and disposed on or in said mat.

9. The system of claim 1, wherein said oxygenation probe comprises an area of about one centimeter.

10. The system of claim 1, wherein said plurality of light sources of said secondary probe are located about one centimeter from said oxygenation probe.

11. The system of claim 1, wherein said light sources of said secondary array are configured to emit light in the near infrared portion of the electromagnetic spectrum.

12. The system of claim 11, wherein said light sources of said secondary array are configured to emit at least two different wavelengths of light.

13. The system of claim 12, wherein a first wavelength is 730 nm and a second wavelength is 850 nm.

14. The system of claim 1, further comprising a computer processor in signal communication with an analysis module, a memory and an input/output module, wherein said input/output module is in signal communication with said plurality of sensor arrays.

15. The system of claim 14, wherein said analysis module is configured to differentiate ulcerous foot tissue from surrounding healthy foot tissue.

16. A method for predicting an occurrence of a diabetic foot ulcer, comprising:
    providing the system of claim 1;
    receiving the bottom portion of said human subject's foot upon said mat;
    generating a map of measured oxygenation on the plantar, mid-foot or heel region of said foot utilizing the system of claim 1;
    identifying, from said map, target regions of potential ulceration in said foot measured by said plurality of oxygenation probes; and
    interrogating said target regions of potential ulceration by generating a map of oxyhemoglobin within said foot utilizing said secondary probes.

17. The method of claim 16, further comprising determining an estimated difference index in oxyhemoglobin concentration between an area probed by said oxygenation probe and an area probed by said secondary probe.

18. The method of claim 17, wherein:
    if the estimated difference index is a positive value, an area of inflammation or hyperperfusion is identified; or
    if the estimated difference index is a negative value, an ischemic or hypervascularization condition is identified.

19. The method of claim 17, wherein said system further comprises a plurality of temperature sensors, and wherein said temperature sensors are utilized to determine regions of temperature asymmetry between the feet of said human subject.

20. The method of claim 19, wherein if a region of temperature asymmetry is determined, utilizing said region as an initial target for generating said map of oxyhemoglobin within said foot.

* * * * *